United States Patent
Ko et al.

(10) Patent No.: US 9,763,990 B2
(45) Date of Patent: Sep. 19, 2017

(54) **METHOD TO PREPARE *GANODERMA LUCIDUM* POLYSACCHARIDES POSSESSING PROTECTIVE ACTIVITIES ON FATTY LIVER DISEASE**

(71) Applicant: Chang Gung Biotechnology Corp., Taipei (TW)

(72) Inventors: Yun-Fei Ko, Taipei (TW); Jan Martel, Taipei (TW); Jian-Ching Liau, Taipei (TW); I-Te Chang, Taipei (TW); Wei-Ting Jian, Taipei (TW); Mei-Feng Lin, Taipei (TW); Chia-Jen Yang, Taipei (TW); Chen-Yaw Chiu, Taipei (TW); Chih-Jung Chang, Taipei (TW); Chuan-Sheng Lin, Taipei (TW); Tsung-Ru Wu, Taipei (TW); Chia-Chen Lu, Taipei (TW); David Marcelo Ojcius, Taipei (TW); Hsin-Chih Lai, Taipei (TW); John D. Young, Taipei (TW)

(73) Assignee: Chang Gung Biotechnology Corp., Taipei (TW)

( * ) Notice: Subject to any disclaimer, the term of this patent is extended or adjusted under 35 U.S.C. 154(b) by 51 days.

(21) Appl. No.: 14/863,130

(22) Filed: Sep. 23, 2015

(65) Prior Publication Data

US 2017/0028003 A1    Feb. 2, 2017

(30) Foreign Application Priority Data

Jul. 27, 2015    (TW) .............................. 104124285 A (51) Int. Cl.
*A61K 36/074*   (2006.01)
*A61K 31/715*   (2006.01)
*C08B 37/00*    (2006.01)

(52) U.S. Cl.
CPC .......... *A61K 36/074* (2013.01); *A61K 31/715* (2013.01); *C08B 37/0003* (2013.01); *A61K 2236/00* (2013.01)

(58) Field of Classification Search
CPC ............................ A61K 31/715; A61K 36/074
See application file for complete search history.

(56) References Cited

PUBLICATIONS

Mayo Clinic, Nonalcoholic fatty liver disease web page, http://www.mayoclinic.org/diseasesconditions/nonalcoholicfattyliverdisease, accessed online on Mar. 1, 2017.*
WebMD, Fatty liver disease web page, http://www.webmd.com/hepatitis/fattyliverdisease, accessed online on Mar. 1, 2017.*
Definition of prevent, Oxford English Dictionary Online, http://dictionary.oed.com/, accessed online Mar. 27, 2010, especially definition 9a. at p. 2.*
Zhang et al., Acta Pharmacol. Sin., 2004, 25(2), p. 191-195.*
Xiao et al., Arch. Pharm. Res., 2012, 35(10), p. 1793-1801.*
Marchesini et al., Diabetes, 2001, 50, p. 1844-1850.*
Sun et al., Carbohydr. Polym., 2014, 114, p. 432-439.*
Zhao et al., Carbohydr. Polym., 2010, 80, p. 783-789.*
Chih-Jung Chang et al, Ganoderma lucidum reduces obesity in mice by modulating the composition of the gut microbiota, Nature Communications |6:7489 |DOI: 10.1038/ncomms8489.

* cited by examiner

*Primary Examiner* — Jonathan S Lau
(74) *Attorney, Agent, or Firm* — WPAT, P.C., Intellectual Property Attorneys; Anthony King (57) ABSTRACT

The present invention provides a method to prepare polysaccharides from *Ganoderma lucidum*. The prepared polysaccharides can reduce liver weight and liver lipid content in humans and animals. The prepared polysaccharides can therefore be used to prevent and treat fatty liver disease.

7 Claims, 6 Drawing Sheets

METHOD TO PREPARE *GANODERMA LUCIDUM* POLYSACCHARIDES POSSESSING PROTECTIVE ACTIVITIES ON FATTY LIVER DISEASE

CROSS-REFERENCE TO RELATED APPLICATION

This application claims priority of Taiwan patent application No. 104124285, filed on Jul. 27, 2015, the content of which is incorporated herein in its entirety by reference.

BACKGROUND OF THE INVENTION

1. Field of the Invention

The present invention relates to compositions and methods for preventing and treating fatty liver disease. Particularly, the present invention provides methods for preventing and treating fatty liver disease by using polysaccharides isolated from *Ganoderma lucidum* as well as methods for preparing the polysaccharides.

2. The Prior Art

Fatty liver disease is a condition in which large vacuoles of triglycerides accumulate in the liver. This condition occurs mostly in the liver of alcoholic and obese individuals. Fatty liver disease is often associated with inflammation, a condition termed steatohepatitis. In the long term, fatty liver disease may lead to several complications, including liver cirrhosis, hepatocellular carcinoma, and death. The high prevalence of fatty liver disease is currently a major threat to public health, with an estimated 10 to 24% of the human population being affected worldwide. Prevention and treatment of this disease thus represents a major challenge.

Traditional Chinese medicine has a long history in Asian countries dating back several thousands of years. One class of traditional remedies commonly in use consists of medicinal mushrooms such as *Antrodia cinnamomea*, *Agaricus blazei* Murrill, *Ganoderma lucidum*, and *Ophiocordyceps sinensis*. These mushrooms contain a wide range of immuno-modulatory and bioactive compounds. The medicinal mushroom *G. lucidum* has been used for centuries to promote health and longevity. Yet, it is unclear whether *G. lucidum* or any of its components may produce beneficial effects on fatty liver disease.

In view of the growing incidence of fatty liver disease in the human population and the difficulties observed in prevention and treatment, there is a need for alternative measures to prevent, treat and control this condition. New measures that can be introduced in the diet without requiring considerable changes in lifestyle and without incurring in toxicity or adverse effects on health are particularly needed.

SUMMARY OF THE INVENTION

The present invention provides a method for preventing or treating fatty liver disease comprising the administration of an effective amount of a polysaccharide extracted from *Ganoderma lucidum* to a subject, wherein the polysaccharide has a molecular weight above 135 kDa and contains at least mannose, glucose, and galactose.

In one embodiment of the present invention, the polysaccharide further contains fucose, rhamnose, arabinose and glucosamine.

In one embodiment of the present invention, the weight ratio of fucose, rhamnose, arabinose, glucosamine, galactose, glucose, and mannose in the polysaccharide ranges between 2:2:2:1:16:26:47 and 3:3:3:1:17:27:48.

In one embodiment of the present invention, the molecular weight of the polysaccharide ranges from 135 kDa to 5,364 kDa, with a polydispersity index (Mw/Mn) of 6.25, and the average molecular weight of the polysaccharide is 846 kDa.

The *G. lucidum* polysaccharide of the present invention reduces liver weight and liver lipid level in a subject. In one embodiment of the present invention, the effective amount of the polysaccharide given is from 0.001 mg/kg to 1 g/kg per day. Preferably, the effective daily amount or dosage of *G. lucidum* polysaccharide given to a human subject (with an average weight of 70 kg) is 4.53 g (0.0646 g per kilogram of body weight).

The present invention also provides a method to prepare the polysaccharide isolated from *G. lucidum*, comprising the following steps: extracting *G. lucidum* mycelium with water; inducing the formation of a precipitate by adding an alcohol; isolating the precipitate by centrifugation; and fractionating the precipitate to obtain a *G. lucidum* polysaccharide. Specifically, the invention provides a method comprising: (a) mixing the *G. lucidum* mycelium with water to give a first mixture, extracting the first mixture for a first predetermined time under a low-speed rotation to give a supernatant, and concentrating the supernatant to obtain a concentrated *G. lucidum* extract; (b) adding an alcohol to the concentrated *G. lucidum* extract to give a second mixture, allowing the second mixture to stand for a second predetermined time and produce a precipitate to obtain a crude *G. lucidum* polysaccharide extract; and (c) isolating the crude *G. lucidum* polysaccharide extract by centrifugation, and fractionating the crude polysaccharide extract using tangential flow filtration (TFF) to obtain a *G. lucidum* polysaccharide.

In one embodiment of the present invention, for step (a), the *G. lucidum* mycelium is mixed with water at a ratio of 5% (w/v); for step (b), the alcohol comprises 95% ethanol, each volume of the concentrated *G. lucidum* water extract is mixed with 5 volumes of 95% ethanol and the second predetermined time is at least 16 hours; for step (c), comprises fractionating the crude *G. lucidum* polysaccharide extract using tangential flow filtration with a 0.2-μm hollow fiber membrane and a 10 to 300-kDa cassette membrane (50 cm$^2$).

The *G. lucidum* polysaccharide of the present invention can reduce liver weight and liver lipid level in humans and animals. Therefore, the polysaccharide can be used as a drug, health supplement or food for preventing or treating fatty liver disease.

BRIEF DESCRIPTION OF THE DRAWINGS

The nature of the present invention will be apparent to those skilled in the art by reading the following detailed description of the preferred embodiments, with reference to the attached drawings:

FIGS. 6A-6C show the effects of *G. lucidum* polysaccharide sub-fractions on the liver of mice fed a high-fat diet. Eight-week-old male mice of the C57BL/6NCrlBltw genetic lineage were randomly distributed into ten groups containing five animals each. Mice were fed for two months with either a standard chow diet (13.5% of energy from fat) or a high-fat diet (60% of energy from fat), plus daily administration of 100 µl of either water or polysaccharide sub-fraction (G1 to G4) by intragastric gavage. FIG. 6A shows Mice were sacrificed and liver weight was determined. FIG. 6B shows liver tissues were stained with oil red O (ORO) lipid staining. FIG. 6C shows the level of staining was quantified using the Image J software. Polysaccharide sub-fractions G1 and G2 reduced liver weight and lipid levels in HFD-fed mice. Statistical significance was analyzed using Student's t test ($P<0.01$, *$P<0.001$). Scale bars: 30 nm.

DETAILED DESCRIPTION OF THE PREFERRED EMBODIMENT

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

The "effective amount" described in the present invention represents the amount of polysaccharide fraction isolated from *Ganoderma lucidum* that can reduce body weight and fat accumulation in animals and humans. The effective amount may vary depending on the organism or individual treated but can be determined experimentally using various techniques, including a dose escalation study.

The data shown in the present disclosure represent approximated experimental values that can vary within a range of ±20%, preferably ±10%, and most preferably ±5%.

The present invention provides *G. lucidum* polysaccharide having a molecular weight above 135 kDa which is able to prevent or treat fatty liver disease, and the embodiments below show that the *G. lucidum* polysaccharides of the present invention reduce liver weight and liver lipid level of a subject. Generally, the polysaccharides of the present invention can be given to mammals and humans at a dose of 0.001-1,000 mg/kg of body weight per day. The details of the invention are given below.

Characterization of the *G. lucidum* polysaccharide of the present invention is presented first, followed by experimentations showing that the isolated *G. lucidum* polysaccharide sub-fractions reduce signs of fatty liver disease.

EXAMPLE 1

Preparation of the Polysaccharide Fraction Isolated from *G. lucidum*

In the present invention, the *G. lucidum* polysaccharides can effectively reduce liver weight and liver lipid level. The *G. lucidum* polysaccharide of the present invention can be added to the diet of the subject as a drug, a drink, a daily supplement, or a food, without incurring in significant lifestyle changes, toxicity or other unfavorable health conditions.

1.1 Preparation of the Concentrated Water Extract of *G. lucidum*

Figure 1:
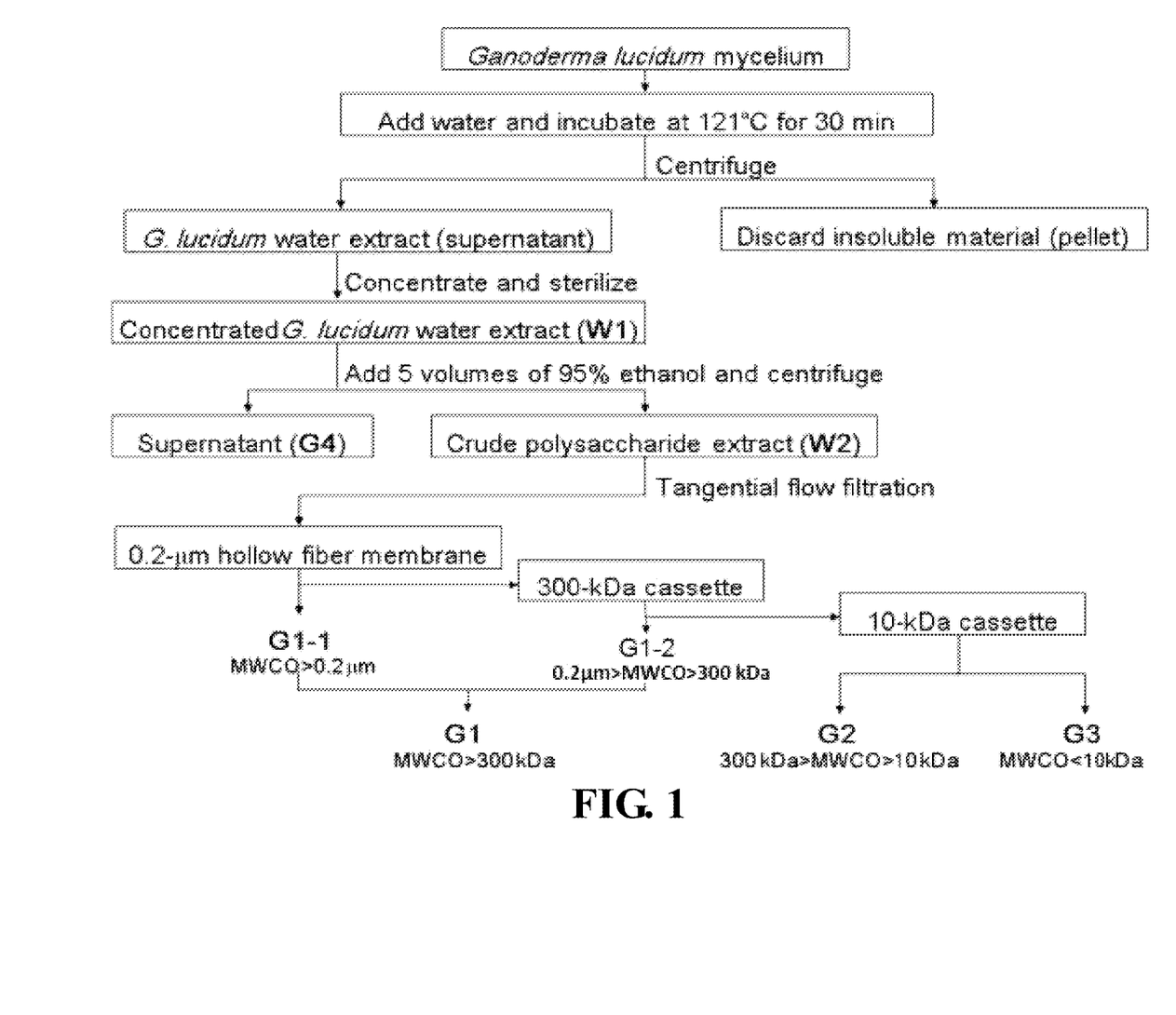
FIG. 1 shows a simplified flowchart for the isolation of *Ganoderma lucidum* water extracts and polysaccharide sub-fractions described in the present invention.

As shown in FIG. 1, a mixture is prepared by mixing 500 g of dried *G. lucidum* mycelium obtained from Chang Gung Biotechnology (Taipei, Taiwan) into 10 liters of distilled water using a 20 liter-stirred tank reactor. The 5% (w/v) mixture is agitated at a speed of 150 revolutions per minute (RPM) for 30 mm at 121° C. The mixture is then centrifuged to remove insoluble material and obtain a supernatant (*G. lucidum* water extract). The supernatant is concentrated to a final volume of 2.5 liters using a vacuum concentrator. The concentrated supernatant is sterilized at high temperature and pressure for 20 mm in an autoclave to obtain a 20% (w/v) concentrated *G. lucidum* water extract (labeled W1) and stored at 4° C. prior to use.

1.2 Preparation of the *G. lucidum* Crude Polysaccharide Extract

As shown in FIG. 1, 120 mL of the W1 20% (w/v) concentrated *G. lucidum* water extract (which contains 6.03 g of total water-soluble carbohydrates; see Table 1) is mixed with 5 volumes (600 mL) of 95% ethanol and incubated at 4° C. for 16 hours to induce the precipitation of crude polysaccharide. The mixture is centrifuged to obtain a supernatant and a precipitate (pellet). The supernatant is removed, while 120 mL of 70% ice-cold ethanol is used to wash and resuspend the precipitate to obtain a mixture. The mixture is centrifuged to obtain a supernatant and a precipitate (pellet). The supernatants from three such washing-resuspension-centrifugation steps are combined to give a supernatant of 1,050 mL (labeled as G4, with total water-soluble carbohydrates of 2.82 g; see Table 1). The crude polysaccharide precipitate (pellet) is dissolved into 1,000 mL of distilled water and concentrated to a final volume of 700 mL using a vacuum concentrator in order to remove residual ethanol. Finally, distilled water is added to obtain a *G. lucidum* crude polysaccharide extract with a final volume of 2,400 mL (labeled as W2, with total water-soluble polysaccharides of 3.21 g; see Tables 1 and 2).

1.3 Fractionation of *G. lucidum* Crude Polysaccharide Extract 2,400 mL of *G. lucidum* crude polysaccharide extract is placed into a beaker, followed by incubation at 50° C. into a water bath. The extract is fractionated by using a tangential flow filtration (TFF) system (KrosFlo, Spectrum Laboratories) with a 0.2-µm hollow fiber membrane (1,500 cm², polyethersulfone, PES). The trans-membrane pressure (TMP) is set at 15-16 psi. 600 mL of distilled water is added into the retentate during filtration. Addition of water is repeated two times (a total of 1,800 mL distilled water is added to the retentate). A 650 mL retentate (labeled as sub-fraction G1-1, total water soluble polysaccharides of 1.26 g) and 3,600 mL of filtrate are obtained this way.

The above-mentioned 3,600 mL of 0.2-µm filtrate is placed into a beaker and incubated at 50° C. in a water bath. The 3,600 mL of filtrate is fractionated by using the TFF system with a 300-kDa cassette membrane (50 cm², PES). The TMP is set between 16-18 psi. 600 mL of distilled water is added into the retentate during filtration when the retentate ranges from 1,000 mL to 1,200 mL. A 950 mL retentate (labeled as sub-fraction G1-2, with total water soluble polysaccharides of 0.60 g) and 3,600 mL filtrate are obtained. Sub-fractions G1-1 and G1-2 are combined to obtain a final sub-fraction of 1,600 mL (labeled as sub-fraction G1; 1.86 g of total water-soluble polysaccharides; see Table 2).

The above-mentioned 3,600 mL of the 300-kDa filtrate is placed into a beaker and incubated at 50° C. in a water bath. The 300-kDa filtrate is fractioned using the TFF system with a 10-kDa cassette membrane (50 cm², PES). The TMP is set between 16-18 psi. 600 mL of distilled water is added into the retentate during filtration when the retentate ranges from 1,000 mL to 1,200 mL. The operation is repeated to obtain 970 mL of 10 kDa-to-300 kDa retentate (labeled as sub-fraction G2; 1.01 g of total water-soluble polysaccharides; see Table 2) and 3,600 mL of 10 kDa filtrate (labeled as sub-fraction G3, 0.34 g of total water-soluble polysaccharides; see Table 2).

The G1, G2, G3 and G4 sub-fractions are concentrated separately using the vacuum concentrator to obtain a final volume of 110 mL. Concentrated sub-fractions are sterilized at high temperature and pressure for 20 min in an autoclave and stored at 4° C. prior to use.

1.4 Total Water-Soluble Carbohydrate and Polysaccharide Content of the Isolated *G. lucidum* Extracts and Sub-Fractions The phenol-sulfuric acid assay is used to determine the level of total water-soluble carbohydrates and polysaccharides found in the isolated *G. lucidum* extracts and polysaccharide sub-fractions, which include the 20% (w/v) concentrated *G. lucidum* water extract (labeled as W1, 120 mL), the *G. lucidum* crude polysaccharide extract (labeled as W2, 2400 mL), a combination of the retentate of the 0.2-μm hollow fiber step and the 300-kDa-cutoff pore membranes (labeled as G1 sub-fraction; 1,600 mL), the retentate of the 10 kDa cassette membrane (labeled as G2 sub-fraction; 970 mL), the filtrate of the 10-kDa-cutoff pore membranes (labeled as G3 sub-fraction; 3,600 mL), and the supernatants of the 95% ethanol precipitation and wash process (labeled as G4 sub-fraction; 1,050 mL). To establish a standard curve for the phenol-sulfuric acid assay, glucose standard solutions are prepared at 0, 0.02, 0.04, 0.06, 0.08, 0.10, 0.12, 0.14, 0.16, 0.18, and 0.20 mg/mL. 200 μL of each solution is placed into 1.5-mL tubes. 200 μL of 5% phenol is added and the solution is mixed. 1 mL of sulfuric acid is added and the solution is mixed. After incubation for 20 min, absorbance is monitored using a spectrophotometer at 490 nm to obtain the calibration curve of glucose standard solutions. The calculated R squared is higher than 0.99. The sample solutions are appropriately diluted and 200 μL of each diluted sample solution is placed into 1.5-mL tubes. Phenol and sulfuric acid are added as described above. After incubation for 20 min, the absorbance is monitored and the value obtained is plotted into the calibration curve of glucose standard solution to determine the concentration of total water-soluble carbohydrates or total water-soluble polysaccharides of the samples.

Total water-soluble carbohydrates and polysaccharides found in the extracts and polysaccharide sub-fractions isolated from *G. lucidum* are shown in Tables 1 and 2. Tables 1 and 2 show that the W2 crude polysaccharide extract isolated from *G. lucidum* contains 3.21 g of water-soluble polysaccharides and that the G1 sub-fraction contains 1.86 g of polysaccharides with a molecular weight above 300 kDa, which accounts for 57.9% of the total polysaccharides found in the crude polysaccharide extract (W2).

TABLE 1

Water-soluble carbohydrates and polysaccharides in the isolated *G. lucidum* extracts

| Fraction | | Content (g) | Percentage (%) |
|---|---|---|---|
| W1 | Total water-soluble carbohydrates | 6.03 | 100 |
| W2 | Total water-soluble polysaccharides | 3.21 | 53.2 |
| G4 | Mono-, di-, oligo-saccharides | 2.82 | 46.8 |

TABLE 2

Polysaccharide distribution of the *G. lucidum* crude polysaccharide extract (W2)

| Fraction | | Content (g) | Percentage (%) |
|---|---|---|---|
| W2 | Total water-soluble carbohydrates | 3.21 | 100 |
| G1 | MWCO > 300 kDa | 1.86 | 57.9 |
| G2 | 300 kDa > MWCO > 10 kDa | 1.01 | 31.5 |
| G3 | 10 kDa > MWCO | 0.34 | 10.6 |

MWCO: molecular weight cut-off 1.5 Monosaccharide Analysis of G1 Polysaccharide Sub-Fraction Isolated from *G. lucidum*

High pH anion exchange chromatography-pulsed amperometric detection (HPAEC-PAD) is used to analyze the monosaccharide components of the G1 sub-fraction. Standard monosaccharide solutions of L-fucose, L-rhamnose, D-galactosamine, D-arabinose, D-glucosamine, D-galactose, D-glucose and D-mannose are prepared at concentrations of 0.1, 0.5, 1, 2, and 5 mg/L. 25 μL of each solution is used for ionic chromatography analysis with the HPAEC-PAD Dionex ICS-5000 System (CarboPacPA1 column with an internal diameter of 4×250 mm, Thermo Scientific). Elution is performed with 16 mM NaOH (which represents a mixture of water and 200 mM NaOH at the volume ratio of 92:8). The flow rate is set at 1 mL/min. The column oven is set at a temperature of 30° C. After 30 min, the peak areas of each monosaccharide standard are determined at 0.1, 0.5, 1, 2, and 5 mg/L. The standard curve of the seven monosaccharide standards is established (calculated $R^2$>0.99).

Figure 2:
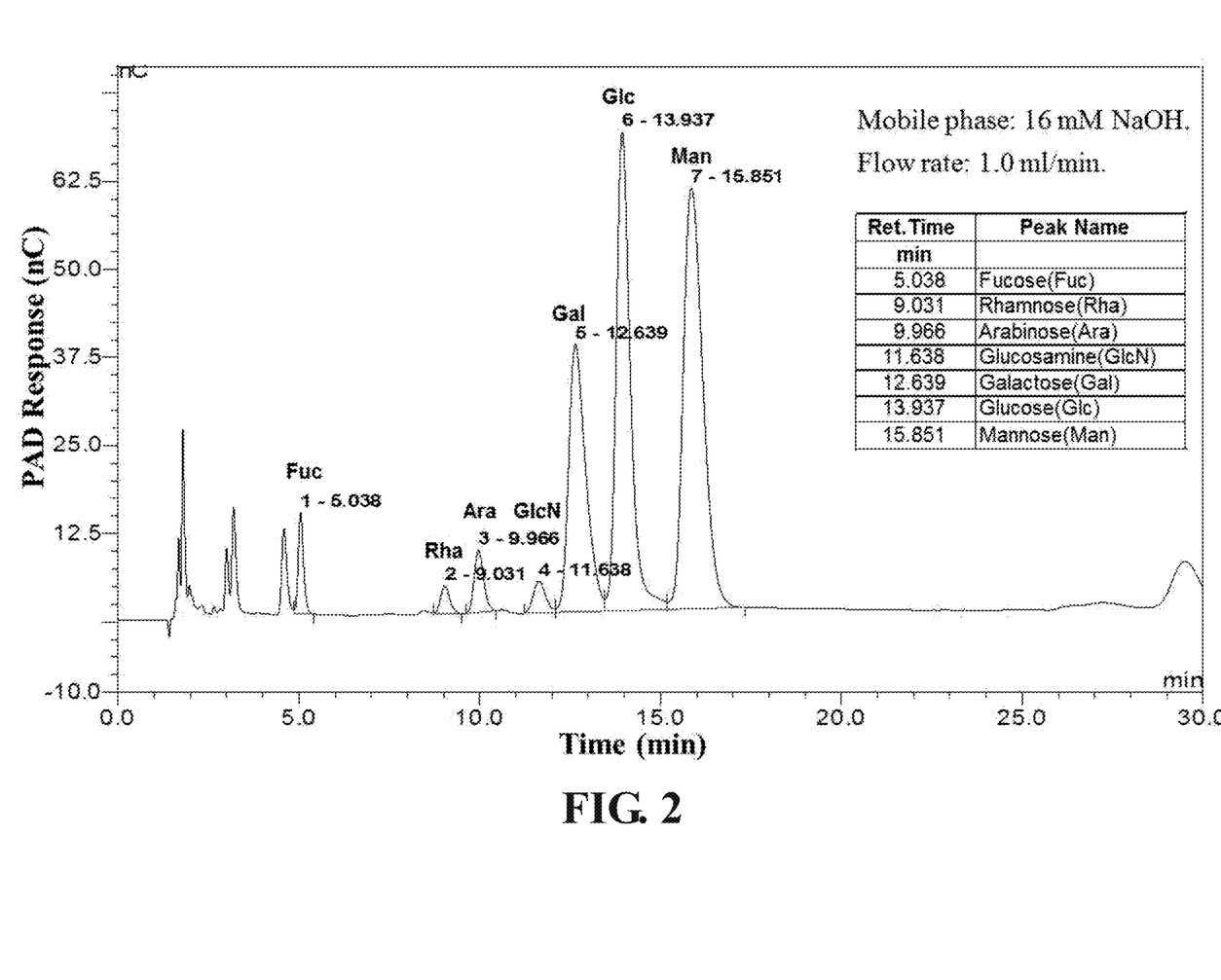
FIG. 2 shows the monosaccharide analysis of *G. lucidum* polysaccharide sub-fraction G1 of the present invention; the analysis was performed using high-performance anion exchange chromatography with pulsed amperometric detection (HPAEC-PAD).

0.21 mL of G1 sub-fraction (3 mg of total water-soluble polysaccharides) is hydrolyzed with 2.79 mL of distilled water and 1.33 mL trifluoroacetic acid at 112° C. in a sealed tube for 12 hours. The acid is removed by co-distillation with water after hydrolysis is completed. Each hydrolysate (1 mg) is dissolved in pure water (1 mg/mL). After a 4-fold dilution of the hydrolysate with pure water (0.25 mg/mL), 25 μL of the hydrolysate solution is used for ionic chromatography analysis using HPAEC-PAD. Elution is performed with 16 mM NaOH as above. After 30 min of analysis, the analytic HPAEC-PAD profile of the hydrolysate solution is acquired. The monosaccharide component and molar ratio of the G1 fraction is determined by comparison with the standard curve. The G1 sub-fraction consists of 2.8% fucose, 2.5% rhamnose, 2.9% arabinose, 1.1% glucosamine, 16.9% galactose, 26.3% glucose, and 47.5% mannose (Tables 3 and 4 and FIG. 2).

TABLE 3

Monosaccharide analysis of the G1 polysaccharide sub-fraction using HPAEC-PAD

| Monosaccharide | Percentage (%) |
| --- | --- |
| Fucose | 2.8 |
| Rhamnose | 2.5 |
| Arabinose | 2.9 |
| Glucosamine | 1.1 |
| Galactose | 16.9 |
| Glucose | 26.3 |
| Mannose | 47.5 |

TABLE 4

Monosaccharide molar ratio of the G1 polysaccharide sub-fraction

| Monosaccharide | Molar ratio |
| --- | --- |
| Fucose | 0.07 |
| Rhamnose | 0.06 |
| Arabinose | 0.07 |
| Glucosamine | 0.02 |
| Galactose | 0.36 |
| Glucose | 0.55 |
| Mannose | 1 |

1.6 Molecular Weight Distribution of the G1 Polysaccharide Sub-Fraction Isolated from *G. lucidum*

The molecular weight of the isolated G1 polysaccharide sub-fraction is analyzed using size-exclusion chromatography (SEC) and high performance liquid chromatography with refractive index (RI), differential viscosity (DV) and light scattering (LS) detectors (with a refractive index detector, Waters model 2410, and a Viscotek 270 dual detector). Dextran 670 (667,800 Da) at 1.5 mg/mL is used as a standard marker to calibrate the system. 100 µL of sample is analyzed on two connected GPC columns (TSKgel G5000PW×L and TSKgel G6000PW×L; 7.8×300 mm). Elution is performed with 0.02% $NaNO_3$ in pure water and the flow rate is set at 0.8 mL/min (column temperature of 22° C.).

Molecular weight analysis of the G1 polysaccharide sub-fraction (total water-soluble polysaccharide of 7.5 mg/mL) is calculated using the OmniSEC software (Viscotek) and the following equations:

Mn: number average molecular weight $$Mn = \frac{\sum NiMi}{\sum Ni}$$

Mw: weight average molecular weight $$Mw = \frac{\sum NiMi^2}{\sum NiMi}$$

Mz: higher average molecular weight $$Mz = \frac{\sum NiMi^3}{\sum NiMi^2}$$

Figure 3:
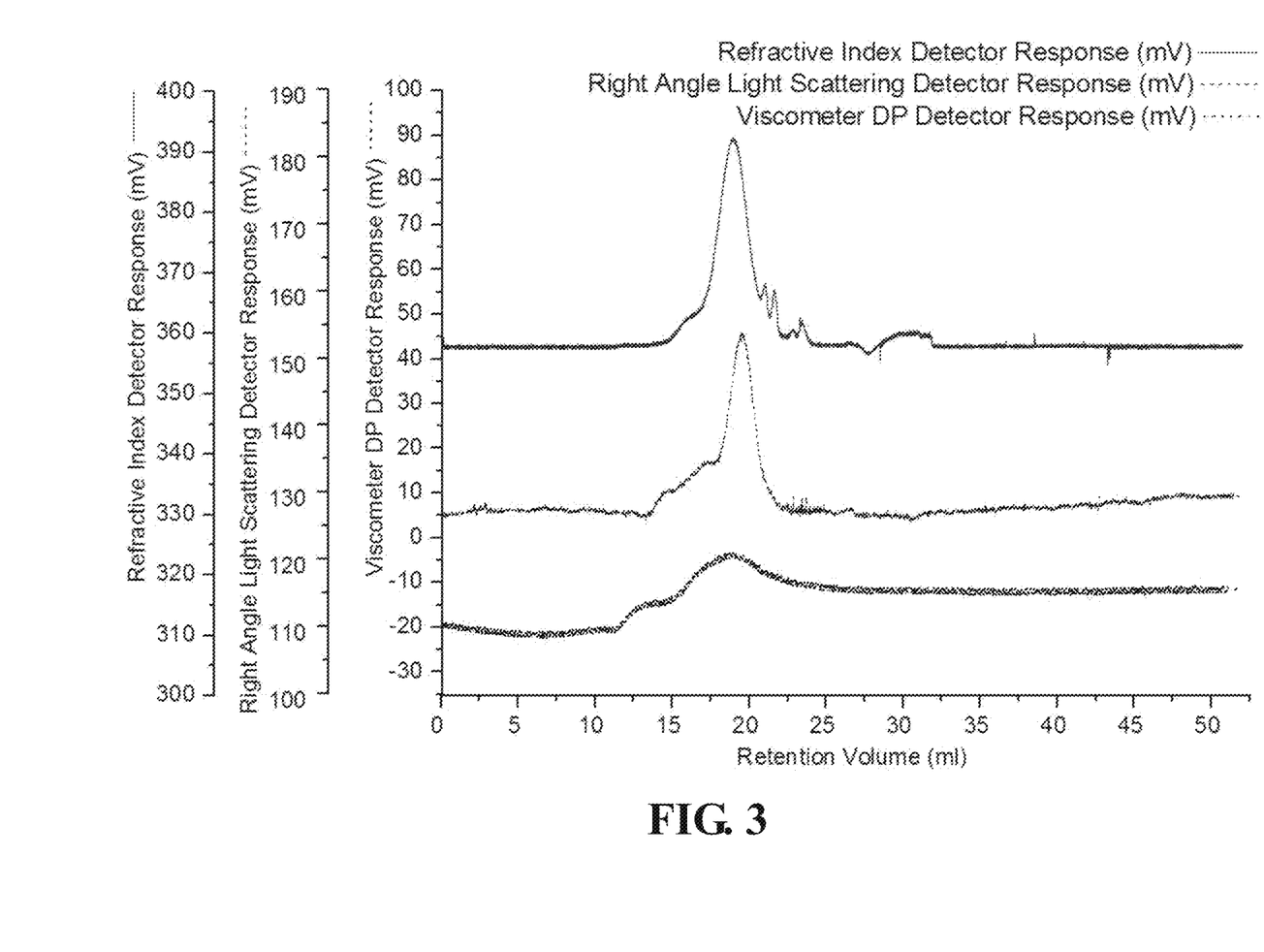
FIG. 3 shows the gel permeation chromatogram of *G. lucidum* polysaccharide sub-fraction G1 of the present invention.
Figure 4:
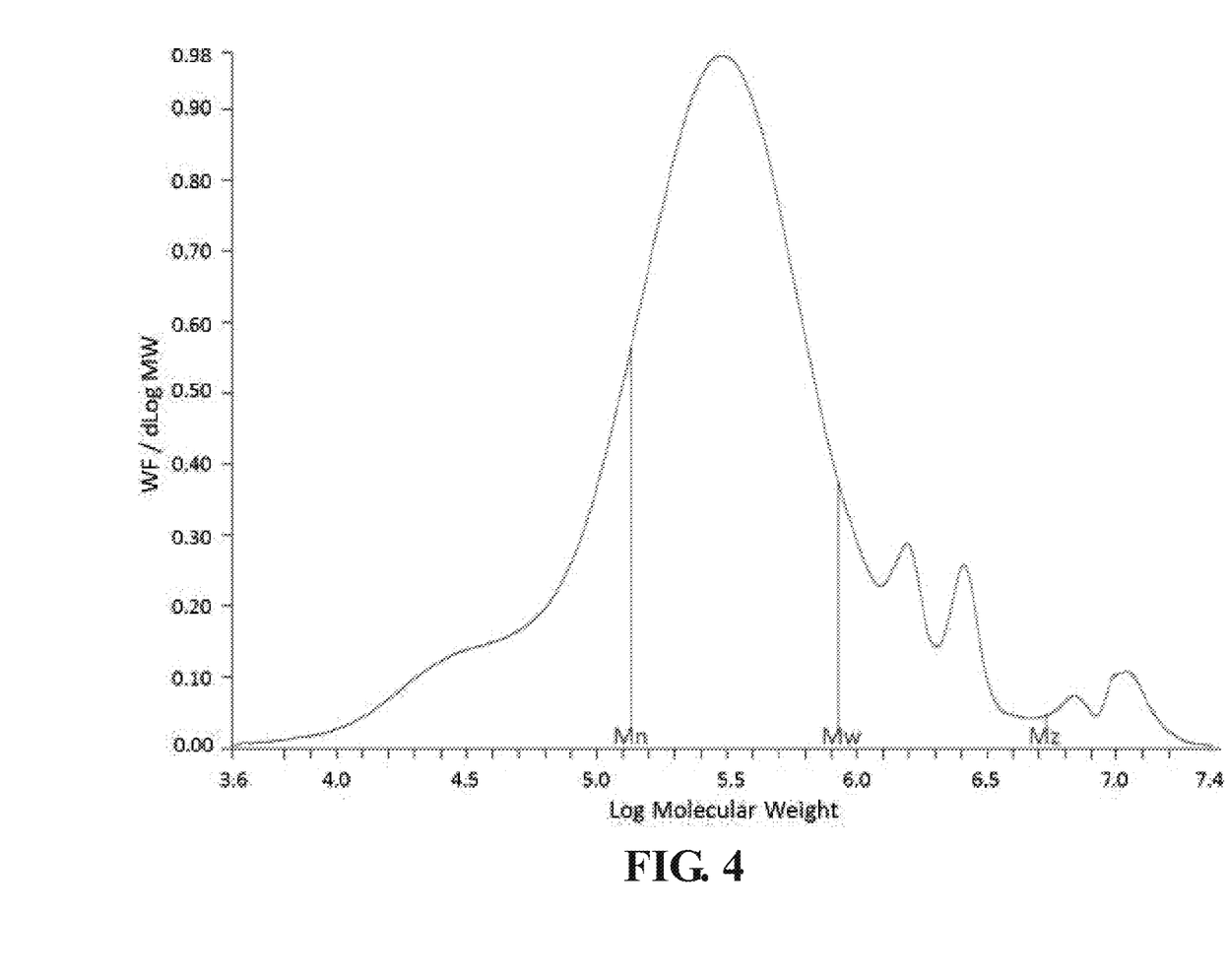
FIG. 4 shows the graph of weight fraction (WF)/d Log molecular weight (MW) vs. log molecular weight (MW) of *G. lucidum* polysaccharide sub-fraction G1 of the present invention.
Figure 5:
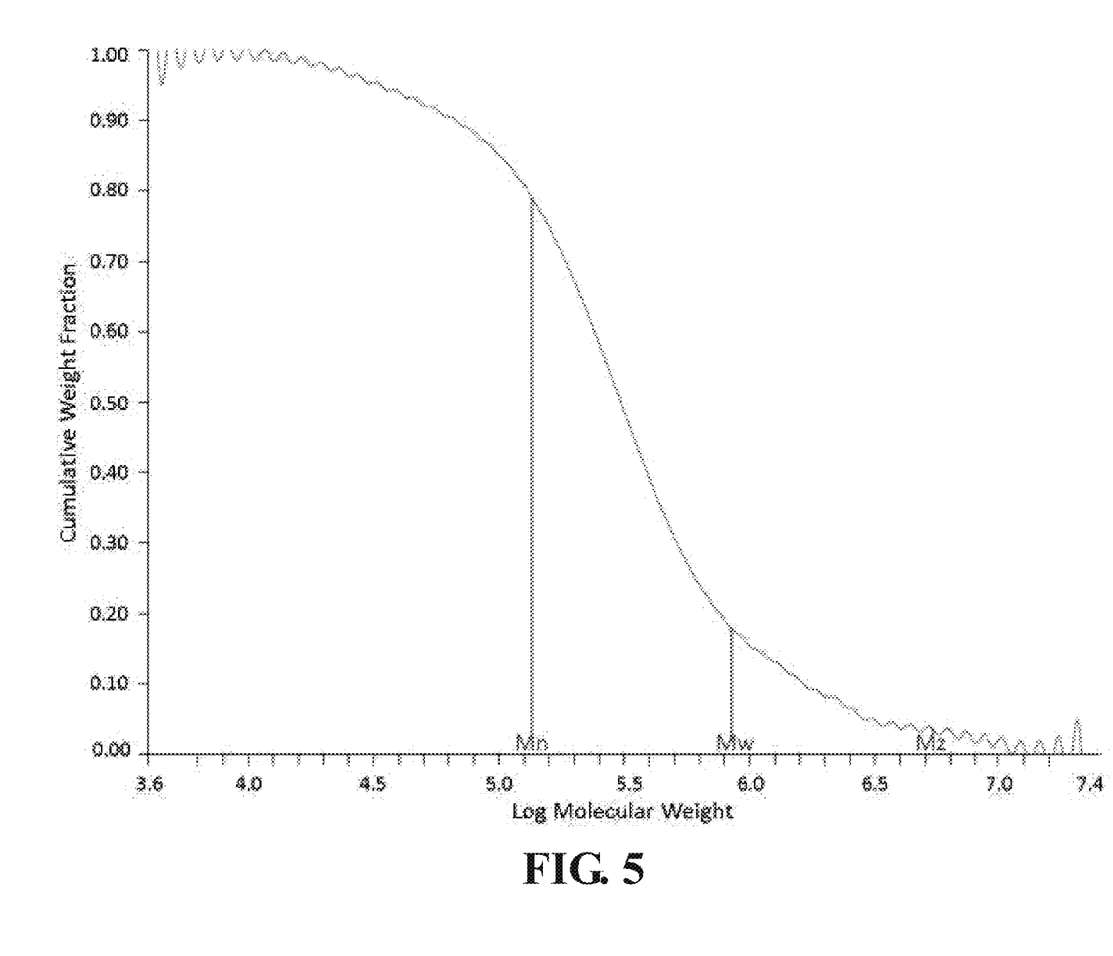
FIG. 5 shows the graph of the cumulative weight fraction vs. log MW of *G. lucidum* polysaccharide sub-fraction G1 of the present invention.

Mp: molecular weight at peak maximum, which is measured at the point of the molecular weight distribution maximum Mi: molecular weight of a chain Ni: number of chains of that molecular weight Based on RI-DV-LS analysis of the G1 sub-fraction (FIG. 3), the molecular weight distribution of this sub-fraction is determined (FIG. 4). Based on these experimental data, the following parameters are calculated: Mn (number average molecular weight), 135,395 Da; Mw (weight average molecular weight), 846,622 Da; Mz (higher average molecular weight), 5,364,000 Da; and Mp (molecular weight at peak maximum), 309,436 Da. The cumulative weight fraction is determined (FIG. 5). Based on these data (FIG. 5), the cumulative weight fraction values of Mn and Mw are 0.79 and 0.18, corresponding to molecular weights of 135,395 Da (Mn) and 846,622 Da (Mw), and a polydispersity index (Mw/Mn) of 6.25, which represents approximately 61% of the total polysaccharide weight.

Even though the G1 polysaccharide sub-fraction isolated from *G. lucidum* represents a retentate obtained with a 300-kDa cut-off membrane, biopolymers such as polysaccharides are known to aggregate under these conditions, an observation which may explain why the calculated molecular weight of the polysaccharides found in the G1 sub-fraction is lower than the molecular weight cut-off of the membranes used to isolate this sub-fraction. Based on the information derived from FIG. 4, the cumulative weight fraction of the G1 sub-fraction described in the present invention has a molecular weight above 135 kDa.

EXAMPLE 2

Figure 6A:
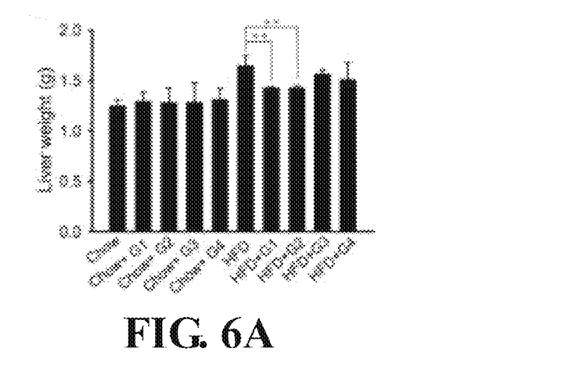
Figure 6B:
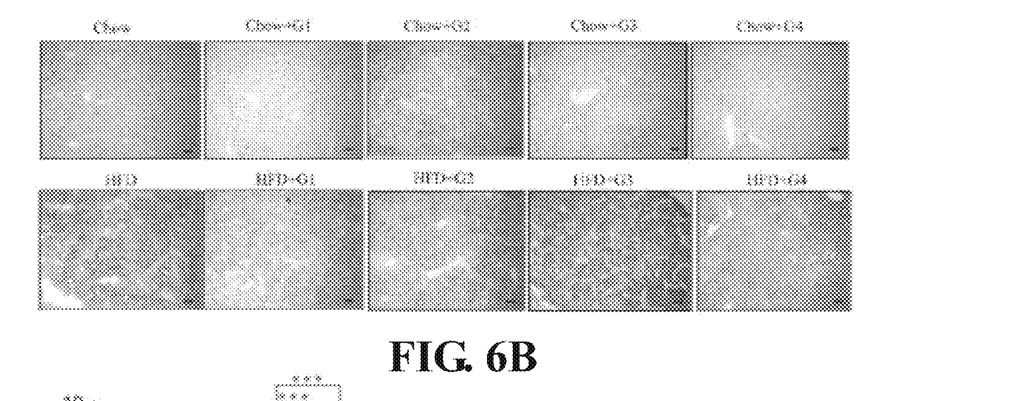
Figure 6C:
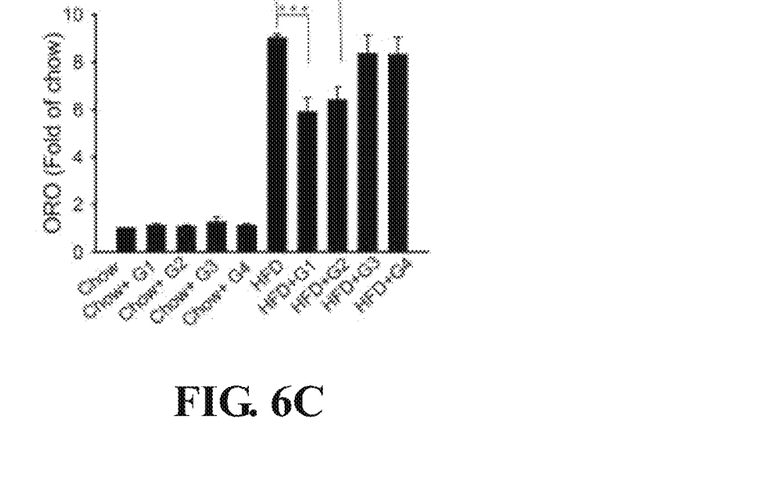

Effects of *G. lucidum* Polysaccharide Sub-Fractions on Body Weight and Fat Accumulation in HFD-Fed Mice In the present invention, C57BL/6NCrlBltw mice are fed with standard chow (13.5% of energy from fat) in the control group (Chow) or with MD (60% of energy from fat) in the experimental group. The mice are also treated daily with 100 µL of polysaccharide sub-fraction (G1, G2, G3, or G4) or distilled water by intragastric gavage for two months (n=5 mice for each group). The animal groups consist of HFD+G1, HFD+G2, HFD+G3, HFD+G4, HFD, Chow+G1, Chow+G2, Chow+G3, Chow+G4, and Chow. Mice were sacrificed and liver weight was determined (FIG. 6A). Liver tissues were stained with oil red O (ORO) lipid staining (FIG. 6B) and the level of staining was quantified using the Image J software (FIG. 6C). Polysaccharide sub-fractions G1 and G2 reduced liver weight and lipid levels in HFD-fed mice.

Treatment of HFD mice with G1 (HFD+G1 group) reduces liver weight (FIG. 6A) more than the other polysaccharide treatments in MD mice. FIG. 6A shows that the liver-weight-reducing effects vary with the molecular weight of *G. lucidum* polysaccharides, and the *G. lucidum* polysaccharides with a molecular weight above 135 kDa (G1 sub-fraction) produce the most significant effects in reducing liver weight. For the liver lipid level, FIGS. 6B and 6C shows that treatment of HFD mice with G1 (HFD+G1 group) reduces liver lipid level more than the other polysaccharide treatments in HFD mice. FIGS. 6B and 6C shows that the liver-lipid-reducing effects vary with the molecular weight of *G. lucidum* polysaccharides, and the *G. lucidum* polysaccharides with a molecular weight above 135 kDa (G1 sub-fraction) produce the most significant effects.

Among all G. lucidum polysaccharide sub-fractions tested in HFD mice, sub-fractions G1 and G2 show statistically significant results in reducing liver weight and lipid level, whereas sub-fractions G3 and G4 show non-significant effects. Polysaccharide sub-fraction G1 produces the best effects in reducing liver weight (FIG. 6A) and lipid levels (FIGS. 6B and 6C) in HFD-fed mice. Given that the polysaccharide content of sub-fraction G1 is 1.94 g/100 mL, the effective daily amount or dosage of G. lucidum polysaccharide required to produce liver-protecting effects in mice (with an average weight of 30 g) is 0.0019 g/mouse (for a period of two months). Accordingly, the effective daily amount or dosage of G. lucidum polysaccharide sub-fraction G1 that would produce similar liver-protecting effects in a human subject (with an average weight of 70 kg) is estimated at 4.53 g/individual, which is equal to 0.0646 g/kg.

The present invention provides G. lucidum polysaccharide sub-fractions, which can reduce signs of fatty liver disease in mammals. The G. lucidum polysaccharide sub-fractions of the present invention are therefore valuable for the development of new preventive strategies and treatments for fatty liver disease. The embodiments presented in the present disclosure are given as representative results that can be obtained with the polysaccharide sub-fractions, but they do not, however, limit the scope of the invention. It will be apparent to those skilled with the art that modifications can be made to the embodiments, without departing from the scope of the present invention and the appended claims.

What is claimed is:

1. A method for treating fatty liver disease, comprising administering an effective amount of a polysaccharide isolated from *Ganoderma lucidum* mycelium to a subject in need thereof, wherein the polysaccharide has a molecular weight above 135 kDa and consists of mannose, glucose, galactose, fucose, rhamnose, arabinose, and glucosamine.

2. The method of claim 1, wherein a weight ratio of fucose, rhamnose, arabinose, glucosamine, galactose, glucose, and mannose in the polysaccharide ranges between 2:2:2:1:16:26:47 and 3:3:3:1:17:27:48.

3. The method of claim 1, wherein the molecular weight of the polysaccharide ranges from 135 kDa to 5,364 kDa, with a polydispersity index (Mw/Mn) of 6.25.

4. The method of claim 1, wherein the average molecular weight of the polysaccharide is 846 kDa.

5. The method of claim 1, wherein the polysaccharide reduces liver weight and liver lipid level of the subject.

6. The method of claim 1, wherein the effective amount of the polysaccharide given is from 0.001 mg/kg to 1 g/kg per day.

7. The method of claim 1, wherein the effective amount of the polysaccharide is 0.0646 g per kilogram of body weight.

* * * * *